United States Patent
Moularat et al.

(10) Patent No.: US 10,344,313 B2
(45) Date of Patent: Jul. 9, 2019

(54) METHOD FOR DETECTING DRY ROT FUNGUS CONTAMINATION

(71) Applicant: CENTRE SCIENTIFIQUE ET TECHNIQUE DU BATIMENT (CSTB), Champs sur Marne (FR)

(72) Inventors: Stéphane Moularat, Lognes (FR); Enric Robine, Conches-sur Gondoire (FR)

(73) Assignee: CENTRE SCIENTIFIQUE ET TECHNIQUE DU BATIMENT (CSTB), Champs sur Marne (FR)

( * ) Notice: Subject to any disclaimer, the term of this patent is extended or adjusted under 35 U.S.C. 154(b) by 0 days.

(21) Appl. No.: 15/519,254

(22) PCT Filed: Oct. 28, 2015

(86) PCT No.: PCT/FR2015/052902
§ 371 (c)(1),
(2) Date: Apr. 14, 2017

(87) PCT Pub. No.: WO2016/066957
PCT Pub. Date: May 6, 2016

(65) Prior Publication Data
US 2017/0233784 A1  Aug. 17, 2017

(30) Foreign Application Priority Data

Oct. 31, 2014 (FR) .................... 14 60498

(51) Int. Cl.
*C12Q 1/04* (2006.01)
*G01N 33/497* (2006.01)

(52) U.S. Cl.
CPC ....... *C12Q 1/04* (2013.01); *G01N 2033/4975* (2013.01); *G01N 2033/4977* (2013.01); *G01N 2333/375* (2013.01)

(58) Field of Classification Search
CPC ..................................................... C12Q 1/04
See application file for complete search history.

(56) References Cited

U.S. PATENT DOCUMENTS

| | | |
|---|---|---|
| 7,131,341 B2 | 11/2006 | Wareham et al. |
| 8,127,593 B2 | 3/2012 | Moularat |
| 9,260,738 B2 | 2/2016 | Moularat et al. |
| 2006/0123931 A1 | 6/2006 | Wareham et al. |
| 2010/0107740 A1 | 5/2010 | Moularat |
| 2014/0080173 A1 | 3/2014 | Moularat et al. |

FOREIGN PATENT DOCUMENTS

| | | |
|---|---|---|
| EP | 2 708 604 | 3/2014 |
| FR | 2 913 501 | 9/2008 |
| GB | 2 401 174 | 11/2004 |

OTHER PUBLICATIONS

Korpi et al. Building and Environment, 1999, 34:205-211.*
Johanningsmeier et al. J of Food Science, 2011, 76:C168-C177.*
International Search Report and Written Opinion of the International Searching Authority dated Dec. 22, 2015, which issued during prosecution of International Application No. PCT/FR2015/052902.
Ewen, et al. "Identification by gas chromatography-mass spectrometry of the volatile organic compounds emitted from the wood-rotting fungi *Serpula lacrymans* and *Coniophora puteana*, and from *Pinus sylvestris* timber" Mycological Research, Jul. 2004, 108(7):806-814.
Hamilton, et al. "Detection of Serpula lacrymans infestation with a polypyrrole sensor array" Sensors and Actuators B: Chemical: International Journal Devoted to Research and Development of Physical and Chemical Transducers, Feb. 2006, 113(2):989-997.
Kuske, et al. "Microbial volatile organic compounds as indicators of fungi. Can an electronic nose detect fungi in indoor environments?" Building and Environment, Jun. 2005, 40(6):824-831.

* cited by examiner

*Primary Examiner* — Bin Shen
(74) *Attorney, Agent, or Firm* — Duane Morris LLP; Thomas J. Kowalski; Deborah L. Lu

(57) ABSTRACT

The invention relates to a method for detecting *Serpula lacrymans* contamination in an internal environment, taking into account the absence and presence of VOCs produced by the metabolism of *Serpula lacrymans*, especially by means of the calculation of a contamination index.

9 Claims, No Drawings

METHOD FOR DETECTING DRY ROT FUNGUS CONTAMINATION

RELATED APPLICATIONS AND INCORPORATION BY REFERENCE

The present patent application is filed pursuant to 35 U.S.C. § 371 as a U.S. National Phase Application of International Patent Application No. PCT/FR2015/052902, which was filed on Oct. 28, 2015, claiming the benefit of priority to French Patent Application No. 14 60498 filed on Oct. 31, 2014. The International Application was published as WO 2016/066957 on May 6, 2016. The contents of each of the aforementioned patent applications are herein incorporated by reference in their entirety.

The present invention relates to a method for detecting dry rot fungus contamination in internal environments.

Dry rot fungus (*Serpula lacrymans*) is a wood-destroying fungus which attacks woods, in particular lumber used as a structure in many buildings. Under conditions favorable to its growth, the colonization of products by this fungus can cause considerable damage while modifying the mechanical properties of the wood. In Northern Europe, dry rot fungus is responsible for 70% of the damage inside buildings, which results in dry rot fungus being considered to be the most harmful agent in a building.

In addition to its involvement in product degradation, the sensitizing role of this fungus has been confirmed, for several years, in atopic and/or asthmatic subjects by means of bronchial provocation tests.

In the light of the extent of this problem, the authorities tend to make it obligatory not only to carry out dry rot fungus contamination detection, but also to report cases of dry rot fungus to the town council.

Today, dry rot fungus contamination is usually detected visually, when the attacked wood shows advanced stages of degradation. Such contamination is counteracted by the removal and replacement of pieces of infested wood and recourse to essentially chemical treatments. In fact, at the current time, there are no means for early detection, in particular when there is not yet any visible sign of contamination, that would enable the implementation of preventive steps.

Based on prior works which resulted in the development of a tool for detecting fungal contaminations and in particular hidden or recent contaminations (FR 2913501), an innovative approach is used herein to detect *Serpula lacrymans* contamination in internal environments. An object of the present invention is thus to overcome all or some of the drawbacks mentioned above.

*Serpula lacrymans*, just like all fungi, emits, from the beginning of its development, volatile molecules (volatile organic compounds) produced either by the metabolism thereof, or from the degradation of the material (or substrate) on which it develops by the enzymes or the acids that it produces. Contrary to spores, these compounds disperse in the environment without being retained by the supports. Consequently, the detection of some of these compounds which are specific for *Serpula lacrymans* makes it possible, on the one hand, to identify a contamination as soon as *Serpula lacrymans* starts to develop and, on the other hand, to detect "masked" contaminations for which there is no visible sign of contamination.

The applicant company has to its credit identified the VOCs emitted by *Serpula lacrymans* during its development. However, the simple detection of the presence of these VOCs results in a large number of false negatives or false positives and thus does not make it possible to sufficiently precisely come to a conclusion regarding a *Serpula lacrymans* contamination. In particular, the development of *Serpula lacrymans* is frequently accompanied by a development of ascomycetes, although the opposite is not true. It is thus important to be able to provide a method for specific detection of *Serpula lacrymans* contamination in order to avoid false positives.

The applicant company has now found that, among the VOCs emitted by *Serpula lacrymans* during its development, some VOCs are present in internal environments only in the presence of *Serpula lacrymans* contamination. These VOCs are thus specific to the development of *Serpula lacrymans*. Conversely, other VOCs emitted by *Serpula lacrymans* during its development may be present in internal environments which do not show any *Serpula lacrymans* contamination. These VOCs are thus not specific to the development of *Serpula lacrymans* and can have other origins, in particular the presence of certain construction materials or else of other biological contaminations such as contaminations with other fungal or bacterial species. Finally, the applicant company has found that some of the VOCs identified as specific to the development of *Serpula lacrymans* are emitted only by certain strains of *Serpula lacrymans*. Consequently, the applicant company has determined three distinct categories of VOCs emitted by *Serpula lacrymans* during its development:

(1) VOCs emitted by *Serpula lacrymans* whatever the *Serpula lacrymans* strain and which do not have other origins;
(2) VOCs emitted by *Serpula lacrymans* whatever the *Serpula lacrymans* strain, but which may have other origins;
(3) VOCs emitted only and specifically by certain *Serpula lacrymans* strains and which do not have other origins.

Thus, the applicant company has to its credit, after thorough research studies, developed a method for detecting *Serpula lacrymans* contamination in an internal environment which allows the detection of such a contamination even in the absence of visible contamination signs.

Thus, the method for detecting *Serpula lacrymans* contamination in an internal environment according to the invention comprises the following steps:
  a. taking a sample of volatile organic compounds (VOCs) from the internal environment,
  b. detecting the presence or absence of predetermined VOCs, emitted by *Serpula lacrymans*, said predetermined VOCs comprising at least one VOC chosen from at least one of the following three VOC categories:
    (1). VOCs emitted by *Serpula lacrymans* whatever the *Serpula lacrymans* strain and which do not have other origins;
    (2). VOCs emitted by *Serpula lacrymans* whatever the *Serpula lacrymans* strain, but which may have other origins;
    (3). VOCs emitted only and specifically by certain *Serpula lacrymans* strains and which do not have other origins;
  c. determining a presence or an absence of *Serpula lacrymans* contamination as a function respectively of the presence and of the absence of said predetermined VOCs, taking into consideration each of the following conditions (i), (ii) and (iii):
(i). the presence of VOCs of category (1) directly indicates the presence of *Serpula lacrymans* contamination, while the absence of such VOCs indicates the absence of *Serpula lacrymans* contamination; and (ii). the presence of VOCs of category (2) does not make it possible to reach a conclusion regarding *Serpula lacrymans* contamination, whereas the absence of such VOCs indicates the absence of *Serpula lacrymans* contamination; and (iii). the presence of VOCs of category (3) indicates the presence of *Serpula lacrymans* contamination, whereas their absence does not make it possible to reach a conclusion regarding the absence of *Serpula lacrymans* contamination.

The term "internal environment" is intended to mean a room confined inside a building or a natural cavity. The internal environment may be continuously aerated (for example by forced ventilation) or non-continuously aerated. Examples of internal environments can be found in buildings such as homes, museums, churches, cellars, historical monuments, administrative buildings, schools and hospitals, but also in natural cavities such as caves.

In the present application, the term "*Serpula lacrymans*" refers to all the *Serpula lacrymans* strains. The term "*Serpula lacrymans* strains" is intended to mean the various genetic variants of the *Serpula lacrymans* species.

The expression "VOCs emitted by *Serpula lacrymans*" is intended to mean the VOCs produced by the metabolism of *Serpula lacrymans*.

The VOCs which can have "other origins" are VOCs that are not specific to the metabolism of *Serpula lacrymans* and can originate for example from construction materials or biological sources such as animals, plants, bacteria or fungi other than *Serpula lacrymans*, in particular ascomycetes.

Step a) of taking the sample of VOCs can be carried out by any technique well known to those skilled in the art. It may be a passive taking of a sample, for example by diffusive sampling on a solid adsorbent of carbograph 4 type. Preferably, the sampling is an active sampling carried out, for example, by means of a pump which forces the passage of ambient air onto a solid absorbent of TENAX™ (rayon) type.

Step b) comprises detecting, from the VOC sample taken in step a), the presence or absence of certain predetermined VOCs, emitted during the development of *Serpula lacrymans*. Said predetermined VOCs are chosen from the following categories (1), (2) and (3):

(1) VOCs emitted by *Serpula lacrymans* whatever the *Serpula lacrymans* strain and which do not have other origins;

(2) VOCs emitted by *Serpula lacrymans* whatever the *Serpula lacrymans* strain, but which may have other origins;

(3) VOCs emitted only and specifically by certain *Serpula lacrymans* strains and which do not have other origins.

Preferably, the predetermined VOCs comprise at least one VOC from each of categories (2) and (3). More preferentially, the predetermined VOCs comprise at least one VOC from each of categories (1), (2) and (3). By detecting the presence or absence of at least one VOC from each of categories (2) and (3), preferentially at least one VOC from each of the three categories (1), (2) and (3), the certainty of the detection method according to the invention is increased with respect to detection of the presence or absence of VOCs from just one of these categories.

Preferably, step b) comprises detecting several VOCs from at least one of the abovementioned categories. More preferentially, step b) comprises detecting several VOCs from at least two of the abovementioned categories, for example at least two VOCs from each of categories (2) and (3). Even more preferentially, step b) comprises detecting several VOCs from each of the abovementioned three categories.

The VOCs of category (1) comprise in particular methyl isocyanide. The VOCs of category (2) comprise in particular 2-methylfuran, 2-methyl-3-butan-2-ol, dimethyl disulfide, furfural, 4-hepten-2-one, alpha-pinene, methyl benzoate and alpha-cubebene. The VOCs of category (3) comprise in particular isobutyronitrile, trichloromethane, methyl thioacetate, 2,5-dimethylfuran, 3-methyl-1,3,5-hexatriene, 2(5H)-furanone, 1-(2-furanyl)ethanone, 3-methylphenyl methylcarbamate, 1-methoxy-3-methylbutane, 5-hepten-2-one, 4-methyl-5-hexen-2-ol, 3-methyl-3-buten-1-ol acetate, benzyl alcohol and 3-iodo-1-propene.

In one particular embodiment, the VOCs of category (1) consist of methyl isocyanide; the VOCs of category (2) consist of 2-methyl-3-butan-2-ol, furfural, 4-hepten-2-one, methyl benzoate and alpha-cubebene; and the VOCs of category (3) consist of isobutyronitrile, trichloromethane, methyl thioacetate, 2,5-dimethylfuran, 3-methyl-1,3,5-hexatriene, 1-(2-furanyl)ethanone, 3-methylphenyl methylcarbamate, 1-methoxy-3-methylbutane, 5-hepten-2-one, 4-methyl-5-hexen-2-ol, 3-methyl-3-buten-1-ol acetate, benzyl alcohol and 3-iodo-1-propene.

Preferably, the presence or absence of the predetermined VOCs is detected by gas chromatography followed by mass spectrometry (GC/MS).

Step c) comprises determining a presence or an absence of *Serpula lacrymans* contamination as a function respectively of the presence and of the absence of said predetermined VOCs, taking into consideration each of the following conditions (i), (ii) and (iii):

(i). the presence of VOCs of category (1) directly indicates the presence of *Serpula lacrymans* contamination, whereas the absence of such VOCs indicates the absence of *Serpula lacrymans* contamination; and (ii). the presence of VOCs of category (2) does not make it possible to reach a conclusion regarding *Serpula lacrymans* contamination, whereas the absence of such VOCs indicates the absence of *Serpula lacrymans* contamination; and (iii). the presence of VOCs of category (3) indicates the presence of *Serpula lacrymans* contamination, whereas their absence does not make it possible to reach a conclusion regarding the absence of *Serpula lacrymans* contamination.

Contrary to the conventional methods using the detection of VOCs, the method according to the present invention takes into account not only the presence of the predetermined VOCs, but also the absence thereof. Thus, the method according to the invention makes it possible to determine with greater certainty the presence or absence of *Serpula lacrymans* contamination.

The determining of a presence or an absence of *Serpula lacrymans* contamination can advantageously be carried out by means of the calculation of a contamination index which is based on the classification of the predetermined VOCs in groups (1), (2) and (3), and on the indication of the presence or absence of each of the predetermined VOCs with regard to the presence or absence of *Serpula lacrymans* contamination.

Thus, step c) of the method according to the invention preferably comprises:

C1) assigning a value to each of the predetermined VOCs as a function of the presence or absence of said predetermined VOC, taking into consideration conditions (i), (ii) and (iii), and C2) calculating a *Serpula lacrymans* contamination index corresponding to the sum of these values, the presence of *Serpula lacrymans* contamination being detected when the contamination index is above a predetermined threshold value.

Typically, the assigning of the values in step c1) is carried out according to a scale of values V1, V2 and V3, in which:

V1 corresponds to an indication regarding the presence of *Serpula lacrymans* contamination;

V2 corresponds to it being impossible to reach a conclusion regarding *Serpula lacrymans* contamination; and V3 corresponds to an indication regarding the absence of *Serpula lacrymans* contamination.

Thus, the presence of a VOC is incremented by a value "V1" if the presence of the VOC indicates the presence of fungal contamination and by a value "V2" if the presence of the VOC does not make it possible to conclude that fungal contamination is present. The absence of a VOC is incremented by a value "V3" if the absence of the VOC indicates the absence of fungal contamination and by a value "V2" if the absence of the VOC does not make it possible to conclude that fungal contamination is absent. Table 1 below summarizes the principle of assignment of the values to the predetermined VOCs according to a scale of values V1, V2 and V3.

TABLE 1

| Category to which the predetermined VOC belongs | Value assigned | |
|---|---|---|
| | Presence | Absence |
| Category (1) | V1 | V3 |
| Category (2) | V2 | V3 |
| Category (3) | V1 | V2 |

Preferably, V1, V2 and V3 satisfy the relationship:

$$V1 > V2 > V3$$

More preferentially, the distance between the values V1 and V2 is equal to the distance between the values V2 and V3.

In one particular embodiment, V1=−V3 and V2=0.

The contamination index is calculated by adding the values that were assigned to each of the predetermined VOCs as a function of their presence or absence. The result of this addition, that is to say the contamination index, indicates whether *Serpula lacrymans* contamination is present or absent.

The conclusion that *Serpula lacrymans* contamination is present or absent as a function of the value of the contamination index depends on the values given to V1, V2 and V3. For example, when V1, V2 and V3 satisfy the relationship V1>V2>V3, a high value indicates the presence of *Serpula lacrymans* contamination; conversely, a low value excludes it.

More particularly, a contamination index above a predetermined threshold value indicates that *Serpula lacrymans* contamination is present. Conversely, a contamination index below or equal to this predetermined threshold value indicates that *Serpula lacrymans* contamination is absent.

The predetermined threshold value is set as a function of the values V1, V2 and V3. For example, when the distance between the values V1 and V2 is equal to the distance between the values V2 and V3, the predetermined threshold value for the contamination index is preferably V3 multiplied by the number of predetermined VOCs detected.

In one preferred embodiment, V1=+1, V2=0 and V3=−1 and the assigning of the values is carried out in the following way:

the presence of a VOC of category (1) is characterized by the value +1 and its absence by the value −1;

the presence of a VOC of category (2) is characterized by the value 0 and its absence by the value −1;

the presence of a VOC of category (3) is characterized by the value +1 and its absence by the value 0.

Thus, the contamination index is either a negative value, or equal to zero, or a positive value. The threshold value of the contamination index is then zero. Consequently, a contamination index below or equal to zero indicates the absence of *Serpula lacrymans* contamination. Conversely, a strictly positive contamination index indicates the presence of *Serpula lacrymans* contamination.

The method for detecting *Serpula lacrymans* contamination according to the invention is particularly useful for the early detection of such a contamination, that is to say before the appearance of visible signs of contamination. This possibility of early detection is of great importance since significant damage has generally already been caused when the first visible signs of *Serpula lacrymans* contamination appear.

The following implementation example illustrates the present invention, without in any way limiting the scope thereof.

EXAMPLE

In situ VOC samples were taken by active sampling on a solid adsorbent of TENAX™ (rayon). type in various internal environments consisting of seventeen rooms of heritage sites. The sample is taken by means of a pump. The sampler is composed of a cartridge and a pump. The cylindrical cartridge consists of a stainless steel tube which is 90 mm long and has an internal diameter of 5 mm, containing a solid adsorbent (Tenax TA, 200 mg per tube). The sample is taken on site for 1 hour at 150 ml/min. The sampling point is between 0.5 and 1 m high. The majority of the VOCs making up the air in the room are then trapped in the adsorbent.

The tubes containing the adsorbent are transferred into a laboratory analytical system. This system consists of the combination of two techniques:

gas chromatography (GC) used to separate the VOCs,
mass spectrometry (MS) used to identify these compounds.

For each of the seventeen rooms, chromatograms are thus obtained and predetermined VOCs emitted by *Serpula lacrymans* are searched for therein. The predetermined VOCs searched for comprise 1 VOC of category (1), 8 VOCs of category (2) and 15 VOCs of category (3) (see table 2 for the predetermined VOCs and their corresponding category).

A contamination index is then calculated in order to group together all of the information provided by the presence or absence of the predetermined VOCs identified. This contamination index is calculated by assigning the value +1, 0 or −1 to each of the predetermined VOCs in the following way:

the presence of a VOC of category (1) is characterized by the value +1 and its absence by the value −1;

the presence of a VOC of category (2) is characterized by the value 0 and its absence by the value −1;

the presence of a VOC of category (3) is characterized by the value +1 and its absence by the value 0.

According to the construction of this index, a positive value makes it probable that a *Serpula lacrymans* development is present in the room studied; conversely, a negative or zero value excludes it.

The calculation of the contamination index for each of the rooms 1 to 17 is presented in table 2.

Finally, the restored environments exhibit negative contamination index values, showing, on the one hand, the absence of residual compounds and, on the other hand, the absence of interference with the treatments applied. Consequently, the contamination index according to the invention

TABLE 2

| Predetermined VOCs (category) | | Room | | | | | | | | | | | | | | | | |
|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 | 17 |
| ethyl isocyanide | (1) | −1 | −1 | −1 | −1 | 1 | −1 | −1 | −1 | −1 | 1 | −1 | −1 | −1 | −1 | 1 | −1 | −1 |
| 2-methylfuran | (2) | 0 | −1 | −1 | −1 | 0 | 0 | −1 | 0 | 0 | 0 | 0 | 0 | 0 | 0 | 0 | 0 | 0 |
| 2-methyl-3-buten-2-ol | (2) | −1 | −1 | −1 | −1 | −1 | −1 | −1 | 0 | −1 | 0 | 0 | 0 | 0 | −1 | 0 | 0 | −1 |
| dimethyl sulfide | (2) | −1 | 0 | 0 | −1 | 0 | −1 | −1 | −1 | −1 | 0 | −1 | −1 | −1 | 0 | 0 | −1 | −1 |
| furfural | (2) | 0 | −1 | 0 | −1 | 0 | 0 | 0 | 0 | 0 | 0 | 0 | 0 | 0 | 0 | 0 | −1 | 0 |
| 4-hepten-2-one | (2) | 0 | −1 | 0 | −1 | −1 | −1 | −1 | −1 | −1 | 0 | 0 | 0 | −1 | −1 | 0 | −1 | 0 |
| alpha-pinene | (2) | 0 | 0 | 0 | −1 | −1 | 0 | 0 | 0 | 0 | 0 | 0 | 0 | 0 | 0 | 0 | −1 | 0 |
| methyl benzoate | (2) | 0 | 0 | −1 | 0 | 0 | −1 | 0 | −1 | −1 | 0 | 0 | 0 | −1 | 0 | 0 | −1 | 0 |
| alpha-cubebene | (2) | 0 | −1 | 0 | −1 | 0 | −1 | 0 | −1 | 0 | 0 | 0 | 0 | 0 | −1 | −1 | 0 | −1 | 0 |
| isobutyronitrile | (3) | 0 | 0 | 0 | 0 | 0 | 0 | 0 | 0 | 0 | 0 | 0 | 0 | 0 | 0 | 0 | 0 | 0 |
| trichloromethane | (3) | 0 | 1 | 0 | 0 | 0 | 0 | 0 | 1 | 1 | 0 | 1 | 1 | 1 | 1 | 1 | 0 | 1 |
| methyl thioacetate | (3) | 0 | 0 | 0 | 0 | 0 | 0 | 1 | 0 | 0 | 0 | 0 | 0 | 0 | 0 | 1 | 0 | 0 |
| 2,5-dimethylfuran | (3) | 0 | 0 | 0 | 0 | 0 | 0 | 0 | 0 | 0 | 0 | 0 | 1 | 0 | 0 | 0 | 0 | 0 |
| 3-methyl-1,3,5-hexatriene | (3) | 0 | 0 | 0 | 0 | 0 | 0 | 0 | 0 | 0 | 1 | 0 | 0 | 0 | 0 | 0 | 1 | 1 | 1 |
| 2(5H)-furanone | (3) | 1 | 1 | 0 | 1 | 1 | 0 | 0 | 0 | 0 | 1 | 1 | 1 | 1 | 0 | 1 | 0 | 0 |
| 1-(2-furanyl)ethanone | (3) | 0 | 0 | 1 | 0 | 0 | 0 | 0 | 0 | 0 | 0 | 0 | 0 | 0 | 1 | 0 | 0 |
| 3-methylphenyl methylcarbamate | (3) | 0 | 0 | 1 | 0 | 0 | 1 | 0 | 0 | 0 | 0 | 1 | 1 | 0 | 0 | 1 | 0 | 0 |
| 1-methoxy-3-methylbutane | (3) | 0 | 0 | 0 | 0 | 0 | 0 | 0 | 0 | 0 | 0 | 0 | 1 | 0 | 0 | 0 | 0 | 0 |
| 5-hepten-2-one | (3) | 0 | 0 | 0 | 0 | 0 | 0 | 0 | 0 | 0 | 1 | 0 | 0 | 0 | 0 | 0 | 0 | 0 |
| 4-methyl-5-hexen-2-ol | (3) | 0 | 0 | 0 | 0 | 0 | 0 | 0 | 0 | 0 | 0 | 0 | 0 | 0 | 0 | 0 | 0 | 0 |
| 3-methyl-3-buten-1-ol acetate | (3) | 0 | 0 | 0 | 0 | 0 | 0 | 0 | 0 | 0 | 0 | 0 | 0 | 0 | 0 | 0 | 0 | 0 |
| benzyl alcohol | (3) | 0 | 0 | 0 | 0 | 0 | 0 | 0 | 0 | 0 | 0 | 0 | 0 | 0 | 0 | 0 | 0 | 0 |
| 3-iodo-1-propene | (3) | 0 | 0 | 0 | 0 | 0 | 0 | 0 | 0 | 0 | 0 | 0 | 0 | 0 | 0 | 0 | 0 | 0 |
| Contamination index | | −2 | −4 | −2 | −7 | −2 | −4 | −5 | −3 | −3 | 3 | 1 | 3 | −3 | −3 | 7 | −6 | −1 |

The interpretation of the contamination index according to the invention suggests that only rooms 10, 11, 12 and 15, for which the contamination index is positive, show *Serpula lacrymans* contamination.

The seventeen rooms were investigated independently in order to determine their actual state of *Serpula lacrymans* contamination and contamination with other fungi. The seventeen rooms were able to be be classified in four groups as a function of their actual state of contamination:
  eight rooms (rooms 1 to 5, 7, 8 and 14) showed no fungal development (neither dry rot fungus nor ascomycetes);
  four rooms (rooms 10 to 12 and 15) showed dry rot fungus development;
  two rooms (rooms 6 and 17) showed ascomycetes development without dry rot fungus development; and
  three rooms (rooms 9, 13 and 16) had been restored after dry rot fungus contamination by means of chemical and/or physical treatment.

All of the cases of *Serpula lacrymans* contamination in the environments tested were detected with the contamination index according to the invention, whereas the environments not contaminated with *Serpula lacrymans* generated a negative index score. Thus, the contamination index according to the invention produced no false negatives or false positives.

Furthermore, the environments contaminated with ascomycetes (microorganisms which are nevertheless close to *Serpula lacrymans*) but free of *Serpula lacrymans* development remain negative. This observation shows the specificity of the contamination index according to the invention. This specificity, which is essential for limiting the cases of false positives, is all the more significant since the presence of *Serpula lacrymans* is frequently accompanied by ascomycete developments, although the opposite is not true.

can also be used for checking remediations of environments formerly contaminated with *Serpula lacrymans*.

The invention claimed is:

1. A method for detecting and treating *Serpula lacrymans* contamination in an internal environment, comprising the following steps:
   a. taking a sample of volatile organic compounds (VOCs) from the internal environment,
   b. detecting the presence or absence of predetermined VOCs, emitted by *Serpula lacrymans*, said predetermined VOCs comprising at least one VOC chosen from each of the following three VOC categories:
     (1). VOCs emitted by *Serpula lacrymans* whatever the *Serpula lacrymans* strain and which do not have other origins;
     (2). VOCs emitted by *Serpula lacrymans* whatever the *Serpula lacrymans* strain, but which may have other origins;
     (3). VOCs emitted only and specifically by certain *Serpula lacrymans* strains and which do not have other origins wherein
       the VOCs of category (1) consist of methyl isocyanide,
       the VOCs of category (2) are chosen from the group consisting of 2-methylfuran, 2-methyl-3-butan-2-ol, dimethyl disulfide, furfural, 4-hepten-2-one, methyl benzoate and alpha-cubebene,
       the VOCs of category (3) are chosen from the group consisting of isobutyronitrile, trichloro-methane, methyl thioacetate, 2,5-dimethylfuran, 3-methyl-1,3,5-hexatriene, 2(5H)-furanone, 1-(2-furanyl) ethanone, 3-methylphenyl methylcarbamate, 1-methoxy-3-methylbutane, 5-hepten-2-one, 4-methyl-5-hexen-2-ol, 3-methyl-3-buten-1-ol acetate, benzyl alcohol and 3-iodo-1-propene;

c. determining a presence or an absence of *Serpula lacrymans* contamination as a function respectively of the presence and of the absence of said predetermined VOCs, taking into consideration each of the following conditions (i), (ii) and (iii):

(i). the presence of VOCs of category (1) directly indicates the presence of *Serpula lacrymans* contamination, while the absence of such VOCs indicates the absence of *Serpula lacrymans* contamination; and (ii). the presence of VOCs of category (2) does not make it possible to reach a conclusion regarding *Serpula lacrymans* contamination, whereas the absence of such VOCs indicates the absence of *Serpula lacrymans* contamination; and (iii). the presence of VOCs of category (3) indicates the presence of *Serpula lacrymans* contamination, whereas their absence does not make it possible to reach a conclusion regarding the absence of *Serpula lacrymans* contamination; and (d). chemically and/or physically treating the internal environment when *Serpula lacrymans* contamination is detected.

2. The method according to claim 1, wherein said predetermined VOCs comprise at least one VOC from each of categories (2) and (3).

3. The method according to claim 1, wherein said predetermined VOCs comprise at least one VOC from each of categories (1), (2) and (3).

4. The method according to claim 1, wherein step c) comprises

C1) assigning a value to each of the predetermined VOCs as a function of the presence or absence of said predetermined VOC, taking into consideration the conditions (i), (ii) and (iii), and C2) calculating a *Serpula lacrymans* contamination index corresponding to the sum of these values, the presence of *Serpula lacrymans* contamination being detected when the contamination index is above a predetermined threshold value.

5. The method according to claim 4 wherein, in step c1), the assigning of the values is carried out according to a scale of values V1, V2 and V3, in which:

V1 corresponds to an indication regarding the presence of *Serpula lacrymans* contamination;

V2 corresponds to it being impossible to reach a conclusion regarding *Serpula lacrymans* contamination; and V3 corresponds to an indication regarding the absence of *Serpula lacrymans* contamination.

6. The method according to claim 5, wherein V1=+1, V2=0 and V3=−1 and the assigning of the values is carried out in the following way:

the presence of a VOC of category (1) is characterized by the value +1 and its absence by the value −1;

the presence of a VOC of category (2) is characterized by the value 0 and its absence by the value −1;

the presence of a VOC of category (3) is characterized by the value +1 and its absence by the value 0;

a strictly positive index signifying that *Serpula lacrymans* contamination is present and a negative or zero index signifying that *Serpula lacrymans* contamination is absent.

7. A method for detecting volatile organic compounds in an internal environment, comprising the following steps:

a. taking a sample of volatile organic compounds (VOCs) from the internal environment, and b. determining by gas chromatography followed by mass spectrometry the presence or absence of at least 10 volatile organic compounds selected from the group consisting of methyl isocyanide, 2-methylfuran, 2-methyl-3-butan-2-ol, dimethyl disulfide, furfural, 4-hepten-2-one, methyl benzoate, alpha pinene, alpha-cubebene, isobutyronitrile, trichloro-methane, methyl thioacetate, 2,5-dimethylfuran, 3-methyl-1,3,5-hexatriene, 2(5H)-furanone, 1-(2-furanyl)ethanone, 3-methylphenyl methylcarbamate, 1-methoxy-3-methylbutane, 5-hepten-2-one, 4-methyl-5-hexen-2-ol, 3-methyl-3-buten-1-ol acetate, benzyl alcohol and 3-iodo-1-propene.

8. The method of claim 7, wherein at step b, the presence or absence of at least 15 volatile organic compounds are determined.

9. The method of claim 7, wherein at step b, the presence or absence of methyl isocyanide, trichloro-methane, methyl thioacetate, 2,5-dimethylfuran, 3-methyl-1,3,5-hexatriene, 2(5H)-furanone, 1-(2-furanyl)ethanone, 3-methylphenyl methylcarbamate, 1-methoxy-3-methylbutane, 5-hepten-2-one, 4-methyl-5-hexen-2-ol, 3-methyl-3-buten-1-ol acetate, benzyl alcohol and 3-iodo-1-propene are determined.

* * * * *